(12) United States Patent
Fischer et al.

(10) Patent No.: US 9,666,048 B2
(45) Date of Patent: May 30, 2017

(54) SCATTERED LIGHT SMOKE DETECTOR OF THE OPEN TYPE, IN PARTICULAR HAVING A SIDELOOKER LED

(71) Applicant: Siemens Schweiz AG, Zurich (CH)

(72) Inventors: Martin Fischer, Buelach (CH); Thomas Rohrer, Sachseln (CH); Matthias Stutz, Zwillikon (CH)

(73) Assignee: SIEMENS SCHWEIZ AG, Zurich (CH)

( * ) Notice: Subject to any disclaimer, the term of this patent is extended or adjusted under 35 U.S.C. 154(b) by 0 days.

(21) Appl. No.: 14/955,135

(22) Filed: Dec. 1, 2015

(65) Prior Publication Data
US 2016/0343226 A1    Nov. 24, 2016

(30) Foreign Application Priority Data
Dec. 4, 2014    (EP) ..................................... 14196365

(51) Int. Cl.
*G08B 17/107*    (2006.01)
*G01K 1/02*    (2006.01)
*G01N 21/49*    (2006.01)

(52) U.S. Cl.
CPC ........... *G08B 17/107* (2013.01); *G01K 1/024* (2013.01); *G01N 21/49* (2013.01); *G01N 2201/062* (2013.01)

(58) Field of Classification Search
CPC ....... G08B 17/107; G01K 1/024; G01N 21/49
See application file for complete search history.

(56) References Cited

U.S. PATENT DOCUMENTS 7,175,430 B1    2/2007    Gasser et al. .................... 433/37
2016/0116389 A1*    4/2016    Cooper .................. G08B 17/10
356/340

FOREIGN PATENT DOCUMENTS

| DE | 102013003614 A1 | 8/2014 | .......... G08B 17/107 |
| EP | 0926646 A1 | 6/1999 | .......... G08B 17/107 |
| EP | 1039426 A2 | 9/2000 | .......... G08B 17/107 |
| EP | 1191946 A1 | 5/2011 | .............. A61C 9/00 |
| WO | 2004/104959 A2 | 12/2004 | .......... G08B 17/107 |

OTHER PUBLICATIONS

European Search Report, Application No. 14196365.2, 7 pages, Jun. 1, 2015.

* cited by examiner

*Primary Examiner* — Leon Flores
(74) *Attorney, Agent, or Firm* — Slayden Grubert Beard PLLC

(57) ABSTRACT

An open-type scattered light smoke includes a housing shell supporting a circuit substrate having at least one light emitter and one light receiver arranged thereon. The light emitter and the light receiver are arranged in a scattered light array having a scattered light volume located in the open air outside the smoke detector. The light emitter emits a light beam having a direction pay, with part of the path traveled by the directional ray between the light emitter and the scattered light volume running parallel to an outer face of the circuit substrate facing away from the housing shell. The light emitter may be an LED housed in a sidelooker package and the light receiver may be a photodiode housed in a reverse-gullwing package. A sensor surface of the photodiode is aligned opposite the scattered light volume through an opening in the circuit substrate that provides mechanical protection.

17 Claims, 6 Drawing Sheets

SCATTERED LIGHT SMOKE DETECTOR OF THE OPEN TYPE, IN PARTICULAR HAVING A SIDELOOKER LED

CROSS-REFERENCE TO RELATED APPLICATIONS

This application claims priority to EP Application No. 14196365.2 filed Dec. 4, 2014, the contents of which are hereby incorporated by reference in their entirety.

TECHNICAL FIELD

The invention relates to a scattered light smoke detector which has a housing shell and a circuit substrate accommodated thereon. At least one light emitter and one light receiver are arranged on the circuit substrate. The circuit substrate has an inner face disposed opposite the housing shell and an outer face disposed opposite the inner face. The light emitter is embodied for emitting a light beam having a directional ray. The light emitter and the light receiver are arranged in a scattered light array having a scattered light volume located in the open air outside of the scattered light smoke detector.

BACKGROUND

A scattered light smoke detector of the open type having a planar circuit substrate is known from EP 2093734 A1. Arranged on said circuit substrate are a light emitter for emitting an illumination light and also a light receiver mounted adjacent thereto for receiving measured light. The measured light results from a backscattering of the illumination light from for example smoke in a detection space located in the open air outside of the scattered light smoke detector. The light emitter emits the illumination light at right angles to the plane of the circuit substrate. The illumination light is at least partially scattered back in the detection space by approximately 180°, i.e. by between 170° and 190°. The backscattered light then reaches the light receiver as measured light, the main receiving direction of the light receiver likewise being at right angles to the plane of the circuit substrate.

A disadvantageous aspect in the case of said backward-scattered light array is that by far the greatest part of the measured light gets lost. Furthermore, the light receiver has no protection against environmental influences and mechanical effects.

EP 1191496 A1 and EP 1039426 A2 each disclose a scattered light smoke detector of the open type having a light emitter and a light receiver which are arranged in such a way that the scattering point of the light emitter and the light receiver is located outside of the scattered light smoke detector in the open air. Light emitter and light receiver are arranged in a scattered light array at a scattered light angle of approximately 80° to 90°. The main emitting direction of the light emitter and the main receiving direction of the light receiver are therefore inclined relative to one another by this approximately 80° to 90°. When such a scattered light smoke detector is fitted to a mounting surface, typically to the ceiling, the main emitting direction of the light emitter and the main receiving direction of the light receiver are then inclined by approximately 40° to 45° relative to said mounting surface.

As a result of the inclined scattered light array in relation to the mounting surface, the two scattered light smoke detectors of the open type have a comparatively large overall height.

SUMMARY

One embodiment provides a scattered light smoke detector having a housing shell and a circuit substrate accommodated thereon, wherein at least one light emitter and one light receiver are arranged on the circuit substrate, wherein the circuit substrate has an inner face disposed opposite the housing shell and an outer face disposed opposite the inner face, wherein the light emitter is embodied for emitting a light beam having a directional ray, and wherein the light emitter and the light receiver are arranged in a scattered light array having a scattered light volume located in the open air outside of the scattered light smoke detector, wherein a part of the path traveled by the directional ray between light emitter and the scattered light volume runs parallel to the outer face of the circuit substrate.

In a further embodiment, the light emitter is arranged and aligned on the circuit substrate in such a way that the light beam emitted by it runs from the edge of the circuit substrate in the direction of an opposite edge of the circuit substrate.

In a further embodiment, the light receiver is shielded against direct light from the light emitter and wherein its main receiving direction points away from the outer face of the circuit substrate.

In a further embodiment, the light receiver has a sensor surface, wherein an optical window is provided in the circuit substrate for the light receiver and wherein the light receiver is arranged and aligned on the inner face of the circuit substrate in such a way that the sensor surface extends parallel to the inner face of the circuit substrate and is located opposite the optical window such that scattered light from the light emitter can be detected through the optical window acting as an aperture.

In a further embodiment, the light receiver is a photodiode housed in a flip-chip package or housed in a reverse-gullwing package for direct surface mounting on the circuit substrate.

In a further embodiment, the light receiver has a sensor surface, wherein the light receiver is arranged and aligned on the outer face of the circuit substrate in such a way that on the one hand the sensor surface runs parallel to the outer face of the circuit substrate and on the other hand scattered light can be detected by the light emitter.

In a further embodiment, the circuit substrate is provided or embodied for attaching a decorative plate or a decorative film on the outer face of the circuit substrate, and wherein if necessary the decorative plate or the decorative film has cutouts or transparent windows for the light receiver and/or for further optoelectronic components.

In a further embodiment, a direct light receiver is arranged on the circuit substrate, wherein the direct light receiver is aligned to the light emitter for the purpose of detecting direct light, wherein the scattered light volume is located between said light emitter and the direct light receiver, and wherein the direct light receiver is provided for contamination monitoring and/or for monitoring a decrease in brightness of the light emitter.

In a further embodiment, the light receiver is arranged and aligned in an edge region of the circuit substrate and at a scattered light angle to the light emitter, wherein the thus formed scattered light volume is located opposite the outer face of the circuit substrate, and wherein a main receiving direction of the light receiver is parallel to said outer face.

In a further embodiment, the light receiver and/or the direct light receiver is a "sidelooker" photodiode.

In a further embodiment, a direct light receiver is arranged on the circuit substrate, wherein the direct light receiver is aligned to the light emitter for the purpose of detecting direct light from the light emitter, and wherein the scattered light smoke detector has an electronic control and evaluation unit which is connected for signal communication purposes to the light emitter and the direct light receiver and which is configured to activate the light emitter as well as to capture the signal originating from the direct light receiver and to evaluate the same with respect to a sequence of signal jumps having great signal changes, and wherein the control and evaluation unit is configured to compare signal sequences of said type with at least one predefined user-side command sequence and in the event of a valid command sequence to switch over the scattered light smoke detector into an operating mode associated with the command sequence.

In a further embodiment, the scattered light smoke detector has a planar protective cover arranged on the outer face of the circuit substrate for the purpose of covering the circuit substrate, wherein the protective cover is arranged spaced at a distance from the outer face of the circuit substrate such that a light channel for the light beam emitted by the light emitter results between the outer face of the circuit substrate and an oppositely disposed inner face of the protective cover, wherein the protective cover has a cutout for a light outcoupling/funnel element, wherein the light outcoupling/funnel element has a light funnel for the light receiver as well as a light outcoupling part adjoining the same for coupling out the light beam running from the light emitter in the light channel, and wherein the light outcoupling part is embodied in such a way that the coupled-out light beam extends across the light funnel and beyond into the environment of the scattered light smoke detector.

In a further embodiment, the scattered light smoke detector has a planar protective cover provided for covering the circuit substrate and arranged on the outer face of the circuit substrate, wherein the protective cover is arranged spaced at a distance from the outer face of the circuit substrate so that an accommodation space for a light conductor element adjoining the light emitter for forwarding the light beam emitted by the light emitter results between the outer face of the circuit substrate and an oppositely disposed inner face of the protective cover, wherein the protective cover has a cutout for a light outcoupling part of the light conductor element, wherein the light conductor element is embodied in such a way that the light beam running in the light conductor element is coupled out at an exit surface of the light lead-out part and extends across a receiving zone of the light receiver and beyond into the environment of the scattered light smoke detector.

In a further embodiment, the light emitter is a "sidelooker" LED.

In a further embodiment, on the outer face of the circuit substrate at least one first environment light emitter is arranged for emitting light away from the outer face and substantially at right angles to the latter into the environment of the scattered light smoke detector, and/or a plurality of second environment light emitters for emitting light substantially radially away from the scattered light smoke detector into the environment of the scattered light smoke detector are arranged on the outer face of the circuit substrate in a radially outward lying edge region, and the light receiver is arranged on the circuit substrate, the main receiving direction of the light receiver pointing away from the outer face of the circuit substrate and being at right angles thereto, and if necessary a plurality of environment light receivers are arranged on the outer face of the circuit substrate in the radially outward lying edge region for the purpose of detecting environment light from a substantially radial direction toward the scattered light smoke detector, and the scattered light smoke detector has an electronic control and evaluation unit which is connected for signal communication purposes to the environment light emitters and the light receiver as well as where applicable to the environment light receivers, and wherein the control and evaluation unit is configured to activate the respective environment light emitters in order to emit in particular modulated light pulses, and wherein the control and evaluation unit is configured to capture the signals originating from the light receiver and where applicable from the environment light receivers, which signals correlate with the modulated light pulses reflected from objects, to evaluate the same with respect to time, and to issue a warning message if a detected object lies within a predefined distance around the scattered light smoke detector and exceeds a predefined minimum signal level.

In a further embodiment, a heat sensor, in particular a thermopile or microbolometer heat sensor, is arranged on the circuit substrate, wherein the scattered light smoke detector has an electronic control and evaluation unit which is connected to the heat sensor for signal communication purposes and which is configured to evaluate a signal captured by the heat sensor for the presence of flicker frequencies characteristic of open fire and if the same are present to issue a flame alarm.

BRIEF DESCRIPTION OF THE DRAWINGS

The invention and advantageous embodiments of the present invention are explained with reference by way of example to the following figures, in which.

DETAILED DESCRIPTION

Figure 1:
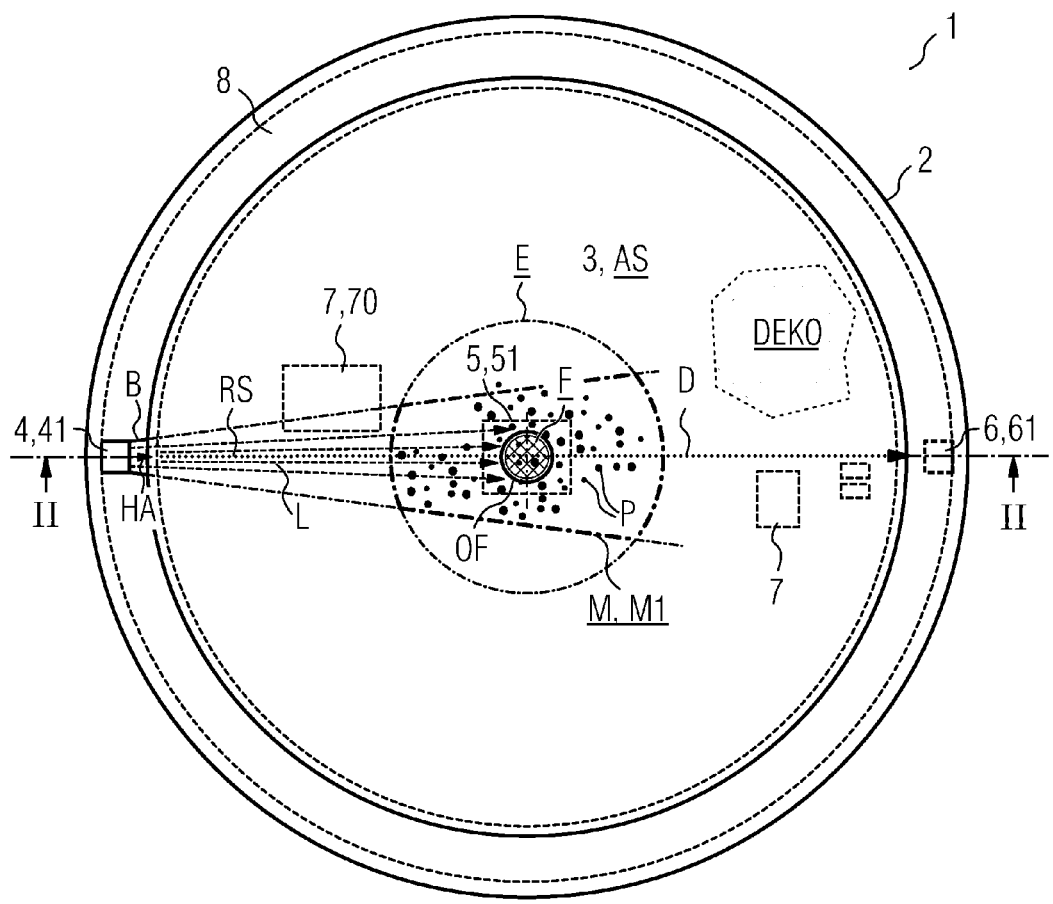
FIG. 1 shows an example of a scattered light smoke detector of the open type having a scattered light array composed of light emitter and light receiver according to the invention.

Embodiments of the invention provide a scattered light smoke detector of the open type which has a particularly simple design and a particularly low overall height.

Some embodiments provide a scattered light smoke detector of the open type in which the optically active surface of the light emitter and of the light receiver is particularly well protected against mechanical effects.

According to embodiments a part of the path traveled by the directional ray between light emitter and the scattered light volume runs parallel to the outer face of the circuit substrate. Preferably a major part of said path traveled, i.e. at least 80%, preferably at least 90%, runs parallel to the outer face. By "parallel", in this context, is meant that a part of the path traveled by said directional ray can also run approximately parallel to the outer face of the circuit substrate, such as e.g. on account of assembly tolerances. Said directional ray can therefore also run at an acute angle of less than 5° to the outer face of the circuit substrate.

The light beam is a parallel, though preferably a divergent light beam. Such a light beam is bounded by peripheral rays. In contrast, the direction of the light beam is specified by the directional ray running in the center of the light beam.

The light emitter is typically a light-emitting diode which preferably emits monochromatic light in a wavelength range of 350 nm to 1000 nm, i.e. in a wavelength range from ultraviolet to infrared.

The photosensor is preferably a semiconductor photodiode. It is optically sensitive to the light emitted by the light emitter.

The at least partial trajectory of the light beam parallel to the circuit substrate advantageously enables the overall height of a scattered light smoke detector of the open type to be significantly reduced.

Compared to the backward-scattered light array according to EP 2093734 A1 cited in the introduction, a significantly greater percentage of measured light or scattered light can be detected by the photosensor, since the particles that are to be detected are illuminated more in the direction leading toward the photosensor.

A further advantage resides in the fact that the light emitter's optically active surface, which is typically arranged at right angles to the circuit substrate and consequently also at right angles to the mounting surface, is now advantageously protected against mechanical effects acting on the scattered light smoke detector of the open type typically in directions leading toward the mounting surface.

According to one embodiment variant the light emitter is arranged and aligned on the circuit substrate in such a way that the light beam emitted by it runs from the edge of the circuit substrate in the direction of an opposite edge of the circuit substrate, i.e. at least roughly toward the (geometric) center of the circuit substrate.

This advantageously enables as great a distance as possible to be realized between the light emitter and the photosensor arranged in the center of the circuit substrate, with the result that the illumination of the scattered light volume, viewed from the standpoint of the light emitter, is effected only in its far field. The term "far field" in this context refers to the portion of the optically active surface of the light emitter or LED that is at a distance of more than 5 cm from it. A largely homogeneous and reproducible light distribution is present in said far field, so the scattered light also exhibits a reliable light distribution in metrological terms.

Due to sources of interference the light distribution in the near field of the light source, on the other hand, exhibits local extinctions, attenuations and increases which are not reliably reproducible. Consequently the scattered light is also likewise subject to these uncertainties. It is for this reason that manufacturers of LEDs specify the light distribution in the far field only.

A further advantage lies in the fact that the light emitter arranged at the (radial) outer edge can also be covered in addition in a constructionally simple manner to protect against mechanical effects by means of a ring-shaped surround or by means of a ring-shaped frame for accommodating the circuit substrate on the scattered light smoke detector (see FIG. 1). A surround of said type for the circuit substrate is typically provided already for mechanical and esthetic reasons.

According to one embodiment variant the light emitter is a so-called "sidelooker LED". An LED of said type is also referred to as a "side-emitting" LED or also as a "side-view" LED. This LED is an SMD component which is embodied for direct surface mounting on a circuit substrate.

The particular advantage in this case is that by means of such a "sidelooker" LED light can be emitted directly and without further optical aids parallel to the circuit substrate. LEDs of this type are produced in high volumes, albeit for entirely different purposes, in particular for illuminating displays and touchscreens from the side. A further advantage is that for that reason such LEDs are embodied already for emitting a narrow light beam of less than 30°.

According to one embodiment variant the light receiver is shielded against direct light from the light emitter. Its main receiving direction points away from the outer face of the circuit substrate. In particular, the main receiving direction is at right angles to the outer face of the circuit substrate.

The light receiver can be shielded against direct light from the light emitter e.g. by means of an aperture which is arranged between light emitter and light receiver on the outer face of the circuit substrate.

According to one embodiment variant the light receiver has a sensor surface. An optical window is provided in the circuit substrate for the light receiver. The light receiver is arranged and aligned on the inner face of the circuit substrate in such a way that the sensor surface runs parallel to the inner face of the circuit substrate and is disposed opposite the optical window, such that scattered light from the light emitter can be detected through the optical window acting as aperture.

In the simplest case the optical window is an opening or bore in the circuit substrate. Where appropriate the opening can be sealed off by means of a transparent protective cover made of plastic or glass. The opening can alternatively be provided with an optical lens made of plastic or glass so that an optically larger capture zone is available for the scattered light that is to be captured.

The particular advantage resides firstly in the aperture effect of the opening on the one hand and in the mechanically protected arrangement of the photosensor "behind" the circuit substrate.

Preferably the light receiver is then a photodiode housed in a flip-chip package or housed in a so-called "reverse-gullwing" package. SMD packaging formats of this type for the photodiode (SMD standing for Surface-Mounted Device) are particularly advantageously suitable for direct surface mounting on the circuit substrate, i.e. for SMT (SMT for Surface-Mounting Technology). In contrast to through-hole technology components, SMD components have no wire bonding leads. They can therefore be soldered directly on the circuit substrate by means of solderable bonding pads.

According to an alternative embodiment variant the light receiver has a sensor surface. The light receiver is arranged and aligned on the outer face of the circuit substrate in such a way that on the one hand the sensor surface runs parallel to the outer face of the circuit substrate and on the other hand scattered light from the light emitter is detectable. In this case it may be necessary to provide an aperture in order to protect against direct light from the light emitter and where appropriate also a transparent protective cover.

According to one embodiment variant the circuit substrate is provided for applying a decorative plate or a decorative film on the outer face of the circuit substrate or is embodied for this purpose. If necessary the decorative plate or decorative film can have cutouts or a transparent window for the light receiver and/or for further optoelectronic components. By "transparent window" in this context is meant that the decorative plate or decorative film is clear or diffusely transparent at the corresponding point.

The particular advantage lies in the fact that the scattered light smoke detector of the open type can be decoratively adapted to suit the external environment of the space. The scattered light smoke detector can in this instance be embodied such that the decorative plate can be e.g. snap-fitted onto the circuit substrate. Decorative film can be e.g. a one-sided adhesive film which can then be affixed to the circuit substrate.

According to one embodiment variant a direct light receiver is arranged on the circuit substrate. The direct light receiver is aligned to the light emitter for the purpose of detecting direct light, the scattered light volume being located between said light emitter and the direct light receiver and the direct light receiver being provided for the purpose of contamination monitoring and/or for monitoring a decrease in brightness of the light emitter.

In other words the direct light receiver is arranged opposite the light emitter. In particular the optical transmit axis of the light emitter and the optical receive axis of the direct light receiver are aligned with one another.

By virtue of this arrangement it is possible on the one hand to detect any contamination in the optical path between light emitter and direct light receiver. If a receiver signal output by the direct light receiver undershoots a predefined minimum level, an appropriate warning message can be issued to alert a user. On the other hand it is advantageously possible to check that the light emitter is functioning correctly. To that end the receiver signal output by the direct light receiver can be used to compensate for aging effects of the light emitter, in particular an LED. Thus, for example, a weakening of the receiver signal, which corresponds to a decrease in brightness, detected by means of the electronic control and evaluation unit can be at least partially compensated for.

As a result a rated sensitivity with regard to smoke detection can advantageously be maintained even in the event of increasing contamination.

Figure 5:
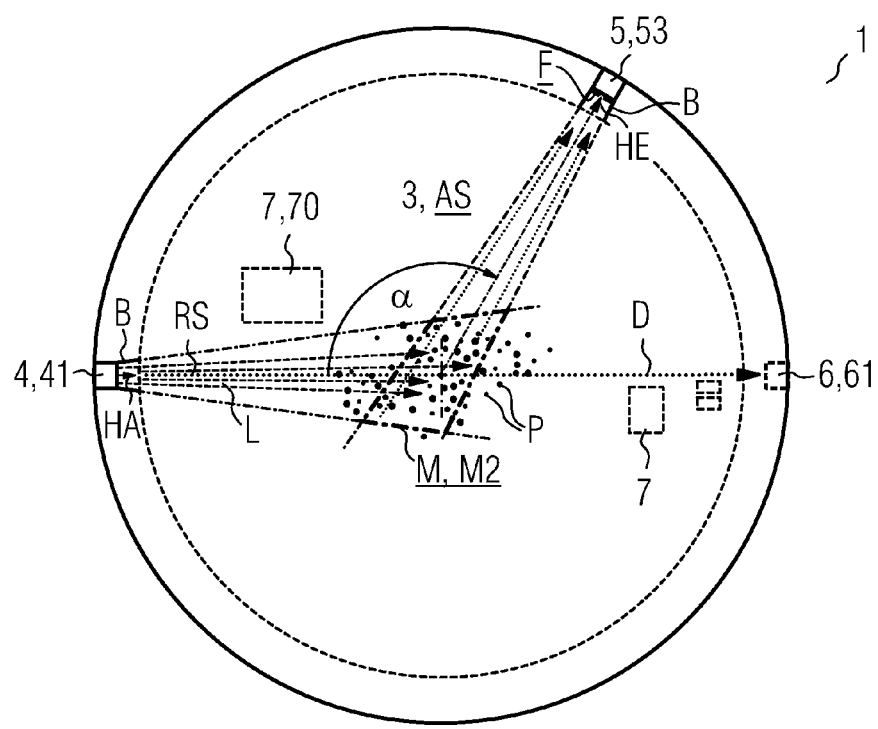
FIG. 5 shows a further embodiment variant having a scattered light array according to the invention arranged on the radial outer edge of the circuit substrate.

Alternatively to the arrangement of the light receiver in roughly the center of the circuit substrate and regardless of whether the same is arranged on the inner or outer face of the circuit substrate, the light receiver can also be arranged and aligned in an edge region of the circuit substrate and at a scattered light angle to the light emitter (see FIG. 5). In this case the thus formed scattered light volume is located opposite the outer face of the circuit substrate and preferably in roughly the center of the circuit substrate. The main receiving direction of the light receiver is in this case not at right angles, but parallel to said outer face.

Preferably both the light emitter and the light receiver are realized as an SMD component and in particular are embodied as a "sidelooker" LED and as a "sidelooker" photodiode, respectively.

The light emitter can also be a two-color "sidelooker" LED. It can be configured for emitting two light beams of monochromatic light at different wavelengths. The two light beams have substantially an identical common directional ray and the only substantial difference between them is their color. The respective emitted light can be e.g. ultraviolet, blue, green, red or infrared light.

In this case of a common scattered light array with the same scattered light angle it is possible to determine the particle size of smoke particles in the scattered light volume by means of the control and evaluation unit using suitable evaluation software. Preferably the emitted light is blue and infrared light. Of course, the aforementioned "sidelooker" LED can also be a multicolor LED such as e.g. an RGB "sidelooker" LED.

According to one embodiment variant a direct light receiver is arranged on the circuit substrate. Said direct light receiver is aligned to the light emitter for the purpose of detecting direct light from the light emitter. The scattered light smoke detector has an electronic control and evaluation unit which is connected to the light emitter and the direct light receiver for signal communication purposes. It is configured for activating the light emitter as well as for capturing the signal originating from the direct light receiver and for evaluating said signal with respect to a sequence of signal jumps exhibiting large signal changes. The control and evaluation unit is additionally configured to compare signal sequences of said type with at least one predefined user-side command sequence and in the event of a valid command sequence to switch over the scattered light smoke detector into a mode of operation associated with the command sequence.

Typically, a scattered light smoke detector already has a control and evaluation unit for activating the light emitter and for evaluating the scattered light detected by the light receiver from smoke particles in order then to issue an alarm if a minimum concentration value of the smoke particles is exceeded. The control and evaluation unit is preferably processor-based and in particular a microcontroller on which a suitable computer program is executed.

What is meant in this context by the user-side input of a command sequence are abrupt interruptions of the light path between light emitter and direct light receiver which come about when a user, such as e.g. a service technician or an apartment owner, interrupts the aforesaid light path with his finger in the manner of pressing a button. Owing to the fact that the finger interrupts the light path virtually completely or releases the same again, the received signal of the direct light receiver has a digital characteristic with signal jumps in a temporal range of a few 100 ms. To that extent such "touch events" can advantageously be detected and interpreted in different ways.

A command sequence can be e.g. a Morse code, such as e.g. "dash-dash-dot" or "dot-dot-dot". A code of said type is unique and can therefore be detected as an unequivocal command sequence by the control and evaluation unit. Alternatively, arbitrary sequences containing binary codes are conceivable, such as e.g. pulse-position codes or pulse-pause codes. A validly captured command sequence can be detected by means of the control and evaluation unit by brief activation of an indicator LED and/or a buzzer of the scattered light smoke detector.

The switchable operating modes of a scattered light smoke detector can have e.g. different functional modes, such as e.g. an alarm triggering profile (sensitive, medium, robust), a volume profile (loud, medium, quiet), environment monitoring (on, off), contamination monitoring (on, off), flame monitoring (on, off) and the like.

A user can therefore advantageously make adjustments to the behavior of the scattered light smoke detector during the operation of the scattered light smoke detector.

According to an alternative embodiment variant the scattered light smoke detector has a planar (light-tight) protective cover provided for the purpose of covering the circuit substrate and arranged on the outer face of the circuit substrate. The protective cover is arranged spaced at a distance from the outer face of the circuit substrate such that a light channel for the light beam emitted by the light emitter results between the outer face of the circuit substrate and an oppositely disposed inner face of the protective cover. The protective cover has a cutout for a light outcoupling/funnel element. The light outcoupling/funnel element has a light funnel for the light receiver as well as a light outcoupling part adjoining the same for coupling out the light beam running from the light emitter in the light channel. The light outcoupling part is embodied in such a way that the coupled-out light beam extends across the light funnel and beyond into the environment of the scattered light smoke detector.

The light channel advantageously affords the light emitter very good protection against mechanical effects as well as against soiling or contamination. The light funnel advantageously serves to enlarge the optical receiving zone. The light emitter is preferably a "sidelooker" LED or "side-emitting" LED.

According to a further alternative embodiment variant the scattered light smoke detector has a planar (light-tight) protective cover provided for the purpose of covering the circuit substrate and arranged on the outer face of the circuit substrate. The protective cover is arranged spaced at a distance from the outer face of the circuit substrate such that an accommodation space for a light conductor element adjoining the light emitter for forwarding the light beam emitted by the light emitter results between the outer face of the circuit substrate and an oppositely disposed inner face of the protective cover. The light conductor element is preferably produced from transparent plastic or glass and is preferably a one-piece component. The protective cover has a cutout for a light outcoupling part of the light conductor element. The light conductor element is embodied in such a way that the light beam running in the light conductor element is coupled out at an exit surface of the light outcoupling part and extends across a receiving zone of the light receiver and beyond into the environment of the scattered light smoke detector.

The light outcoupling part advantageously permits a virtually lossless and directed outcoupling of the light emitted by the light emitter. The light emitter is once again preferably a "sidelooker" LED or a "side-emitting" LED.

According to one embodiment variant at least one first environment light emitter is arranged on the outer face of the circuit substrate for the purpose of emitting light away from the outer face and substantially at right angles to the latter into the environment of the scattered light smoke detector.

Alternatively or in addition thereto, a plurality of second environment light emitters can be arranged on the outer face of the circuit substrate in a radially outward lying edge region for the purpose of emitting light substantially radially away from the scattered light smoke detector into the environment of the scattered light smoke detector.

The light receiver is arranged on the circuit substrate in such a way that its main receiving direction points away from the outer face of the circuit substrate and at right angles to the latter.

Preferably the light receiver is the light receiver or photodiode that is provided or present already for smoke detection. This advantageously removes the need for a separate light receiver.

A plurality of environment light receivers may additionally be arranged on the outer face of the circuit substrate in the radially outward lying edge region for the purpose of detecting environment light from a substantially radial direction toward the scattered light smoke detector.

The scattered light smoke detector has an electronic control and evaluation unit which is connected for signal communication purposes to the environment light emitters and the light receiver as well as where applicable to the environment light receivers. The control and evaluation unit is configured to activate the respective environment light emitters in order to emit in particular modulated light pulses. It is furthermore configured for capturing signals originating from the light receiver and where applicable from the environment light receivers, which signals correlate with the modulated light pulses reflected from objects, evaluating said signals with respect to time, and issuing a warning message if a detected object is located within a predefined distance around the scattered light smoke detector and exceeds a predefined minimum signal level.

By this means a user of the scattered light smoke detector according to the invention is notified if flow-shielding objects are present in the environment of the scattered light smoke detector. In the event of a fire the resulting smoke could possibly no longer reach the scattered light smoke detector.

Independently of the present invention the previous embodiment variant therefore relates to a scattered light smoke detector of the open type. The latter has a circuit substrate having at least one light emitter and one light receiver which are arranged in a scattered light array having a scattered light volume located in the open air outside of the scattered light smoke detector for the purpose of smoke detection. The scattered light smoke detector is provided for mounting on a mounting surface, in particular on a ceiling. The light receiver is arranged and aligned on the circuit substrate in such a way that its main receiving direction points away from the scattered light smoke detector and in the mounted state extends substantially parallel to the surface normal of the mounting surface (see FIG. 2).

Preferably the scattered light smoke detector has an electronic control and evaluation unit that is connected for signal communication purposes to the light emitter and the light receiver. Said unit is provided for activating the light emitter as well as for evaluating the scattered light detected by the light receiver from smoke particles in order to raise an alarm if a minimum concentration value of the smoke particles is exceeded.

The scattered light smoke detector additionally has one or more environment light emitters connected for signal communication purposes to the electronic control and evaluation unit. The latter is configured to activate the at least one environment light emitter in order to emit in particular modulated light pulses and is furthermore configured to capture a receive signal originating from the light receiver which correlates with the modulated light pulses reflected from objects, to evaluate the same with respect to time, and to issue a warning message if a detected object is located within a predefined distance around the scattered light smoke detector and exceeds a predefined minimum signal level.

The light receiver is used both for smoke detection and for environment monitoring. A separate environment light receiver is advantageously not required.

Finally, according to a further embodiment variant, a heat sensor, in particular a thermopile or microbolometer heat sensor, can be arranged on the circuit substrate. The scattered light smoke detector has an electronic control and evaluation unit which is connected for signal communication purposes to the heat sensor and which is configured to evaluate a signal captured by the heat sensor with regard to the presence of flicker frequencies characteristic of open fire and if the same are present to issue a flame alarm.

As a result a fire alarm can be issued instantly in the event of open fire or blazing embers.

FIG. 1 shows an example of a scattered light smoke detector of the open type 1 having a scattered light array composed of light emitter 4, 41 and light receiver 5, 51 according to the invention. The light emitter 4 and also the light receiver 5 are arranged in a scattered light array having a scattered light volume M, M1 located in the open air outside of the smoke detector 1.

In the present example the scattered light smoke detector 1 is embodied in a circular shape. It has a circuit substrate 3, likewise embodied in a circular shape, which is accommodated in a mounting ring 8 as part of a housing shell 2 of the smoke detector 1. In addition to the retaining function it simultaneously serves to protect the light emitter 4, 41 against mechanical effects as well as to protect against soiling and contamination. An outer face of the circuit substrate 3 facing toward the viewer is designated by AS. For decoration purposes the circuit substrate 3 can be provided, as indicated in the drawing, with a decorative film DEKO. The electronic components 7, such as e.g. capacitors, resistors, etc., or microcontroller 70, are preferably applied on an inner face IS of the circuit substrate 3 disposed opposite the visible outer face AS.

The light emitter 4, 41 shown is embodied for emitting a light beam L having a directional ray RS, wherein according to the invention a part of the path traveled by the directional ray RS between light emitter 4, 41 and a scattered light volume M, M1 runs parallel to the outer face AS of the circuit substrate 3. The scattered light volume M, M1 is in this case the geometric intersecting set between an optical receiving zone E of the light receiver 5, 51 and the light beam L. The main radiating direction of the light emitter 41 is further designated by HA, and an aperture for limiting the radiated light beam L at the side by B. The aperture B can also be part of the mounting ring 8.

According to the invention the light emitter 4, 41 is already arranged and aligned on the circuit substrate 3 in such a way that the light beam L emitted by it extends from the edge of the circuit substrate 3 in the direction of an oppositely disposed edge of the circuit substrate 3. The light emitter 4, 41 is accordingly arranged on the outer face AS and in a radially outward lying edge region of the circuit substrate 3. The light emitter 4, 41 is typically an LED. This is configured for emitting typically monochromatic light in a wavelength range from 400 nm to 1000 nm and according to the invention is a "sidelooker" LED or "side-emitting" diode. Also to be seen in this view is the light receiver 5, 51 embodied as a "reverse-gullwing" photodiode, the plane sensor surface F of which is visible according to the invention through an opening OF in the circuit substrate 3. The photosensor 5, 51 "looks", as it were, through the circuit substrate 3 into the scatter area M, M1. It can also at least partially protrude into the opening OF.

Figure 2:
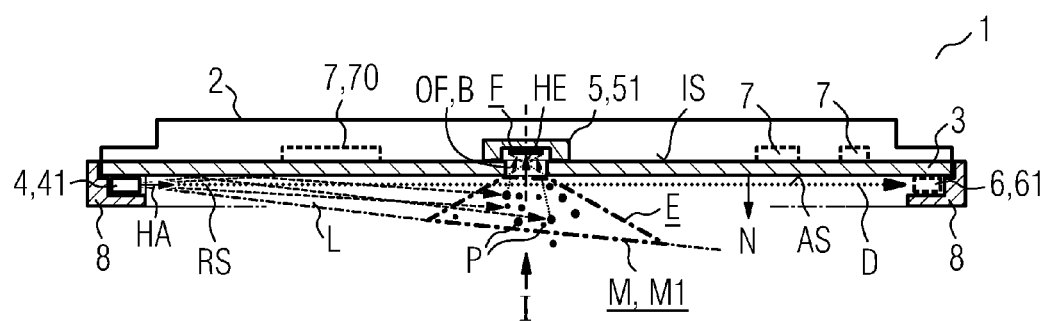
FIG. 2 shows the example according to FIG. 1 in a sectional view along the indicated intersection line II-II.

FIG. 2 shows the example according to FIG. 1 in a sectional view along the indicated intersection line II-II. In this view the scattered light array is particularly clearly recognizable with the embodiment of the scattered light volume M, M1. It can also be seen how the light scattered by smoke particles P passes through the opening OF acting as an aperture B in the circuit substrate 3 to reach the sensor surface F of the reverse-gullwing photodiode 5, 51. The sensor surface F is disposed opposite the opening OF. A main receiving direction of the photodiode 5, 51 pointing away from the outer face AS of the circuit substrate 3 is designated by HE. Said direction runs antiparallel to a normal, labeled N, of the typically plane circuit substrate 3.

Also arranged on the circuit substrate 3 according to the invention is a direct light receiver 6. The latter is aligned to the light emitter 4, 41 for the purpose of detecting direct light D, symbolized by a dotted light ray. As a result of the opposite arrangement to the light emitter 4, 41, the scattered light volume M, M1 is thus also located between light emitter 4, 41 and the direct light receiver 6, 61. This makes contamination monitoring and function monitoring of the light emitter 4, 41 possible by means of the direct light receiver 6, 61.

Figure 3:
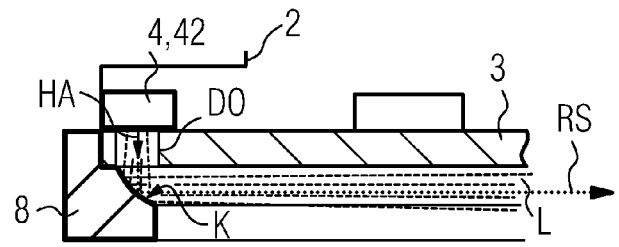
FIG. 3 shows an embodiment variant having a ring-shaped surround for the circuit substrate with optical deflection means according to the invention.

FIG. 3 shows an embodiment variant having a ring-shaped surround 8 for a circuit substrate 3 of the scattered light smoke detector 1 having optical deflection means K according to the invention.

In this case the circuit substrate 3 has a pass-through opening DO for the light emitter 42 in its radial outer edge region. The light emitter 42 is now arranged and aligned on the inner face IS of the circuit substrate 3 in such a way that the light beam L emitted by the light emitter 42 arrives at an optical deflection means K. In the present example the mounting ring 8 embodied for accommodating the circuit substrate 3 has an at least partially circumferential reflecting inner contour K as an optical deflection means K. In this arrangement the optical deflection means K is disposed opposite the pass-through opening DO and deflects the light beam L incident there in such a way that the directional ray RS of the light beam L runs parallel to the outer face AS of the circuit substrate 3. In the present example the light emitter 42 is an LED housed in a flip-chip package for SMD mounting.

Figure 4:
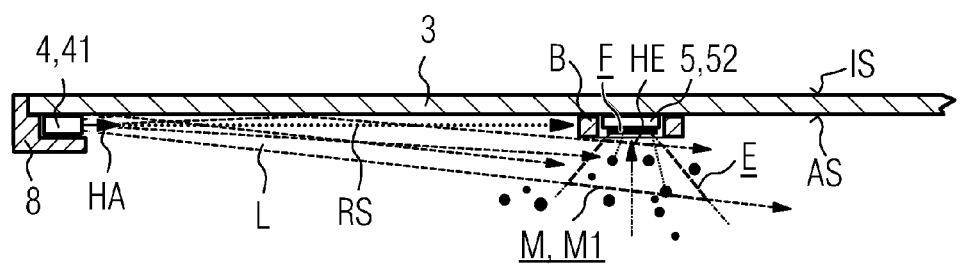
FIG. 4 shows an embodiment variant of the scattered light smoke detector having a light receiver arranged on the circuit substrate outer face with aperture according to the invention.

FIG. 4 shows an embodiment variant of the scattered light smoke detector 1 having a light receiver 5, 52 arranged on the circuit substrate outer face AS with aperture B according to the invention.

In this embodiment variant the light receiver 52 is now arranged and aligned on the outer face AS of the circuit substrate 3 in such a way that on the one hand its sensor surface F runs parallel to the outer face AS of the circuit substrate 3 and on the other hand only scattered light can be detected by the light emitter 41. In order to avoid direct light from the light emitter 41, an aperture B is arranged between light emitter 41 and light receiver 52.

FIG. 5 shows a further embodiment variant having a scattered light array according to the invention arranged on the radial outer edge of the circuit substrate 3.

In this case both the light emitter 4, 41 and the light receiver 5, 53 are arranged in a radial outer region of the circuit substrate 3. They are aligned with respect to one another at a scattered light angle α in such a way that a scattered light volume M2 is (geometrically) defined lying opposite to the outer face AS of the circuit substrate 3. The main emitting direction HA of the light emitter 4, 41 and the main receiving direction HE of the light receiver 5, 53 run parallel to the outer face AS of the circuit substrate 3. In the present example the scattered light volume M2 is defined roughly at the geometric center of the circuit substrate 3.

The scattered light array has a scattered light angle α in a range between 110° and 145°. In the present example it is 120°. In this case the light array is a forward-scattered light array. Alternatively the scattered light array can have a scattered light angle α in a range between 35° to 70°. In such a case the light array is then a backward-scattered light array.

Figure 8:
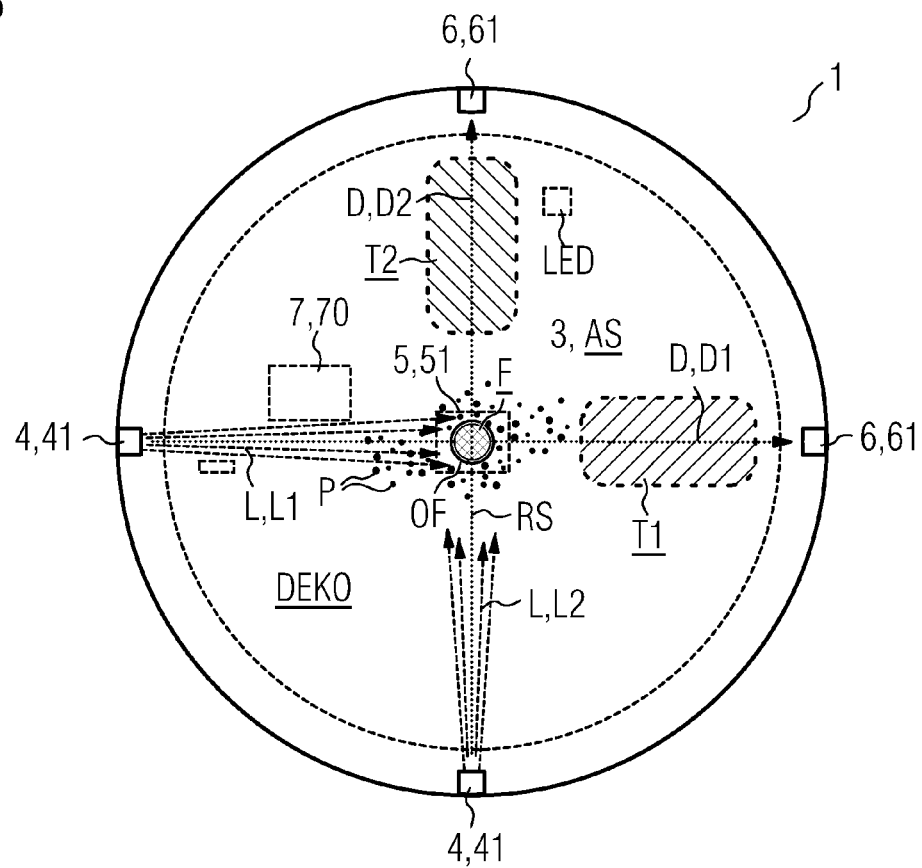
FIG. 8 shows a further embodiment variant of the scattered light smoke detector having a user-side input means according to the invention for changing the operating mode.

The embodiment variant shown in FIG. 5 can furthermore be expanded by means of a second scattered light array (see also FIG. 8 in this regard).

In the case of two light emitters and a single light emitter the scattered light smoke detector can have two scattered light arrays having two forward scatter angles, having two backward scatter angles or having one forward and one backward scatter angle, in each case with a common scattered light center. In other words the main emitting directions of the two light emitters and the main receiving direction of the light receiver then preferably intersect at one point, i.e. in the center of the scattered light volume.

The two light emitters are preferably LEDs. They can emit monochromatic light at the same wavelength or at a different wavelength from one another, such as e.g. blue light, green light, red light or infrared light.

In the case of monochromatic light of different wavelengths and at the same scattered light angle it is then possible for the control and evaluation unit to determine the smoke particle size by means of suitable evaluation software.

In the case of emitted light of identical wavelengths at a different scattered light angle, such as e.g. in the case of a forward-scattered light angle and a backward-scattered light angle, it is then possible for the control and evaluation unit to determine the type of smoke by means of suitable evaluation software.

In the case of two light receivers and a single light emitter the scattered light smoke detector can likewise have once again two scattered light arrays having two forward scatter angles, having two backward-scatter angles or having one forward-scatter and one backward-scatter angle, in each case with a common scattered light center. In other words the main receiving directions of the two light receivers and the main emitting direction of the light emitter then preferably intersect at one point, i.e. in the center of the scattered light volume.

The two light receivers are preferably photodiodes. They can each be sensitive to monochromatic light of different wavelength, such as e.g. to blue light, green light, red light or infrared light, in which case the light emitter 41 then emits at least light having these different wavelengths. The light emitter 41 can be a two-color LED. It can also be a white-light LED.

In this case too, at the same or different scattered light angles, it is possible for the control and evaluation unit to determine the smoke particle size and/or to determine the type of smoke by means of suitable evaluation software.

Figure 6:
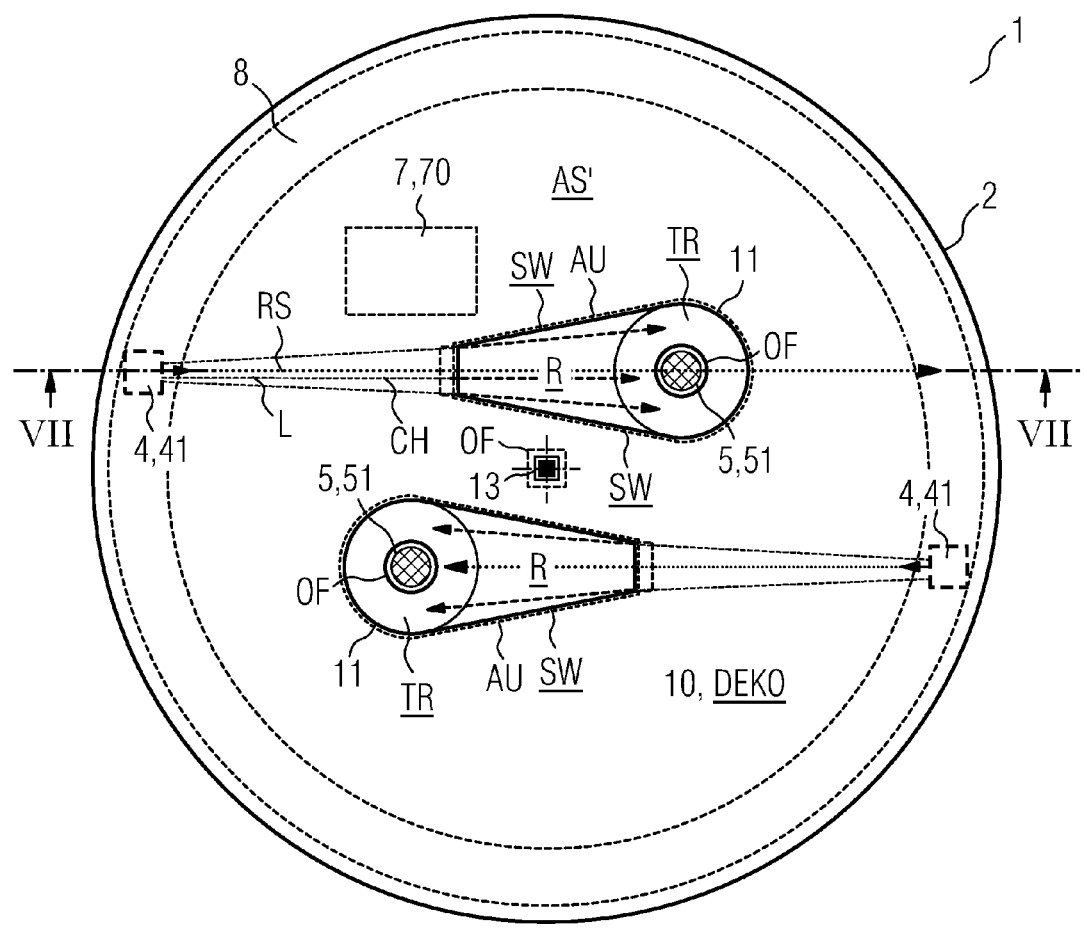
FIG. 6 shows an embodiment variant with protective cover and having a cutout for a light outcoupling/funnel element according to the invention.

FIG. 6 shows an embodiment variant having protective cover 10 and having a cutout AU for a light outcoupling/funnel element 11 according to the invention.

In the present example the scattered light smoke detector 1 shown already has two scattered light arrays, each having a light emitter 41, a light receiver 51 and a light outcoupling/funnel element 11 arranged therebetween in a cutout AU.

In general a double scattered light array enables a higher level of false alarm immunity with regard to malfunctions in one of the two scattered light arrays, such as e.g. caused by flies or insects.

Figure 7:
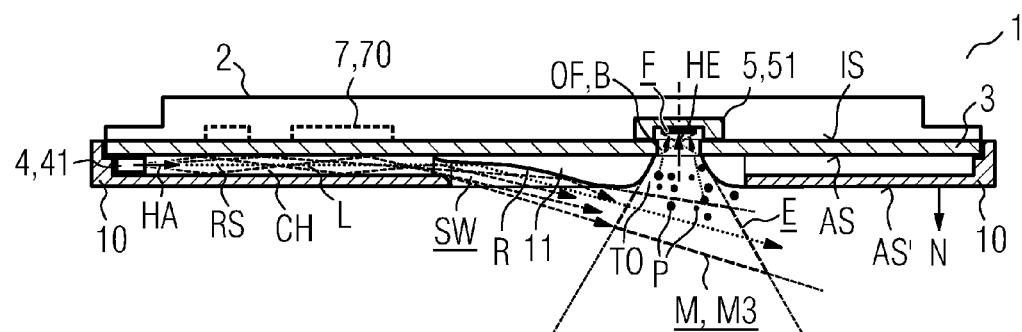
FIG. 7 shows the example according to FIG. 6 in a sectional view along the intersection line VII-VII indicated there.

The view from above onto the illustrated scattered light smoke detector 1 reveals the planar protective cover 10 facing toward the viewer, said cover being arranged spaced at a distance from the outer face AS of the circuit substrate 3 in such a way that a light channel CH for the light beam L emitted by the light emitter 4 results between the outer face AS of the circuit substrate 3 and an oppositely disposed inner face of the protective cover 10 (see also FIG. 7 in this regard). In this case the outer face of the protective cover 10 is designated by AS', and the surface normal of the protective cover 10 which is parallel to the surface normal of the circuit substrate 3 by N. The protective cover 10 is preferably light-tight. At the same time it can be a decorative plate DEKO. Each of the two light outcoupling/funnel elements 11 has a light funnel TR for the light receiver 5, 51 as well as a light outcoupling part R adjoining the same for the purpose of coupling out the light beam L originating from the light emitter 4, 41 and being conducted in the light channel CH. The light outcoupling part R is embodied in such a way that the coupled-out light beam L runs across the light funnel TR and beyond into the environment of the scattered light smoke detector (see FIG. 7 in this regard). The light outcoupling part R is implemented in the manner of a ramp.

Reference sign SW designates two sidewalls which in the present example extend on both sides of the "ramp" and at right angles to the outer face AS' of the protective cover 10. The sidewalls 10 serve equally to provide protection against contaminants. Alternatively the sidewalls can be an integral part of the protective cover 10 itself. Reference sign TO designates the funnel opening, E the optical capture zone of the illustrated arrangement, and 13 a first environment light emitter for implementing environment monitoring. The last-mentioned is explained in the example of FIG. 12 and FIG. 13.

FIG. 7 shows the example according to FIG. 6 in a sectional view along the intersection line VII-VII indicated there.

In this view the trajectory of the light beam L emitted parallel to the outer face AS of the circuit substrate 3 as well as the progression in the light channel CH and the following outcoupling via the light receiver 51 and beyond can be seen in detail. At the same time the light emitter 41 is protected by means of the light-tight protective cover 10 against mechanical effects and contaminants.

FIG. 8 shows a further embodiment variant of the scattered light smoke detector 1 having a user-side input means according to the invention for changing the operating mode.

In the example of the figure shown there the scattered light smoke detector 1 has two scattered light arrays having two light emitters and a common light receiver 51. Both light emitters 41 are configured to emit preferably monochromatic light in wavelength ranges that are different from one another. Preferably one light emitter 41 emits infrared or red light and the other light emitter 41 green, blue or UV light. The light receiver 51 is sensitive to both "light colors". The two light emitters 41 are preferably activated alternately. The control and evaluation unit 70 can then calculate the particle size of the detected smoke particles P from the ratio of the light receiver signal associated with the two light emitters 41 with respect to time in order to determine the type of smoke.

Alternatively both light emitters 41 can also be configured to emit identical monochromatic light. Although with this arrangement an identical scattered light angle is then present in each case between light emitter 41 and light receiver 51, different scattered light volumes are nonetheless present. The two light emitters 41 are in turn preferably activated alternately. The control and evaluation unit 70 is configured to establish, by comparing the two light receiver signals, the presence of disturbance variables, such as e.g. the presence of an insect. This is in particular when the two light receiver signals differ significantly from one another in their amplitude and above all abruptly.

According to the invention a direct light receiver 6 is arranged opposite the respective light emitter 41. In this case the direct light receiver 6 is aligned to the respective light emitter 41 for the purpose of detecting direct light D, D1, D2. The respective light beam running in the direction of the oppositely disposed direct light receiver 61 is designated by L1 and L2. An input field T1, T2, indicated by hatching in the figure, is inserted between the light receiver 51 and the respective direct light receiver 61. The input field T1, T2 can be graphically highlighted as an input means for a user on the outer face AS of the circuit substrate 3 or on the illustrated decorative film DEKO. If a user now touches such an input field T1, T2 with his finger, the light path between light emitter 41 and associated oppositely disposed direct light receiver 61 is interrupted. If the finger is removed, the light path is released once again. The electronic control and evaluation unit 70 is connected for signal communication purposes to the light emitters 41 and the direct light receivers 61. It is configured to activate the respective light emitter 41 as well as to capture the signal originating from the associated direct light receiver 61 and to evaluate said signal for a sequence of signal jumps exhibiting large signal changes. As described in the introduction, a change in the operating mode of the scattered light smoke detector 1 is possible in this way. In the present case there are even two input possibilities available, which can also be combined with one another.

Figure 9:
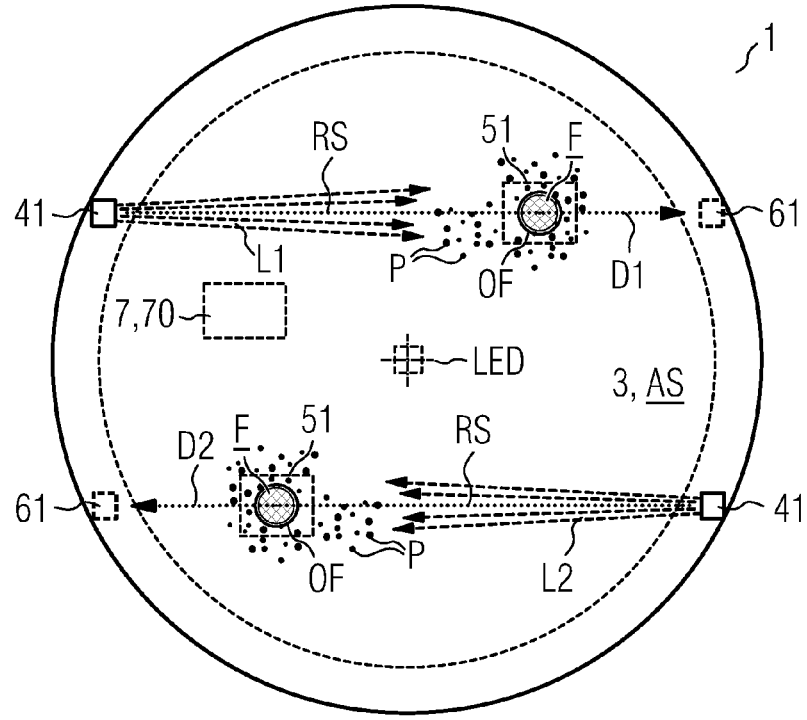
FIG. 9 shows an embodiment variant of the scattered light smoke detector according to FIG. 1 having two scattered light arrays according to the invention.

FIG. 9 shows an embodiment variant of the scattered light smoke detector 1 according to FIG. 1 having two scattered light arrays according to the invention, each having a light emitter 41 and light receiver 61. By this means a higher level of false alarm immunity with regard to malfunctions in one of the two scattered light arrays, such as e.g. caused by flies or insects, is advantageously possible. An indicator light-emitting diode in the manner of a ready-to-operate indication is designated by LED. This indicates the functional readiness of the scattered light smoke detector 1 by repeated brief flashing, such as e.g. every 30 seconds.

Figure 10:
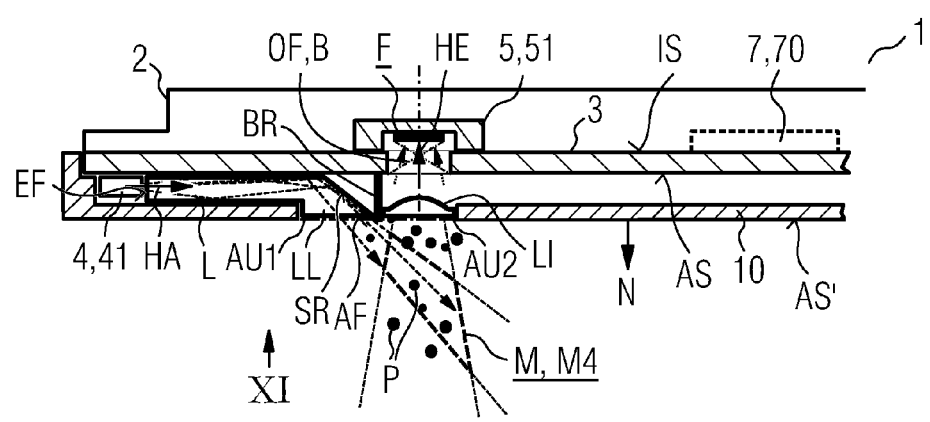
FIG. 10 shows a further embodiment variant of the scattered light smoke detector in a sectional view with a protective cover and having a light conductor element for light outcoupling according to the invention.

FIG. 10 shows a further embodiment variant of the scattered light smoke detector 1 in a sectional view with a protective cover 10 and having a light conductor element LL for coupling out light according to the invention.

The scattered light smoke detector 1 has a planar (light-tight) protective cover 10 spaced at a distance from the outer face AS of the circuit substrate 3. The distance preferably lies in the range of 3 to 10 mm. The spaced-apart arrangement results in an accommodation space for a light conductor element LL adjoining the light emitter 41. The light conductor element LL is provided for forwarding the light beam L emitted by the light emitter 41. It is implemented in the manner of a prism. The light emitter 41 is in turn a sidelooker LED. It is arranged directly opposite the light conductor element LL for the purpose of coupling in the emitted light beam L. It is aligned in such a way that the emitted light beam L is coupled in at right angles into a preferably plane incoupling surface EF of the light conductor element LL.

The protective cover 10 also has a (first) cutout AU1 for a light outcoupling part AT of the light conductor element LL. The light conductor element LL is in this case embodied in such a way that the light beam L running in the light conductor element LL is coupled out at an exit surface AF of the light outcoupling part AT. Inside the light conductor element LL, a part of the light beam L impinges on an inclined surface SR such that said part is reflected with total internal reflection in the direction of the exit surface AF. The light conductor element LL is preferably flush with the outer face A' of the protective cover 10. The exit surface AF is furthermore preferably embodied as plane. The coupled-out light beam L then runs further via a receiving zone E of the light receiver 51 and beyond into the environment of the scattered light smoke detector 1.

Adjacent to the first cutout AU1 in the protective cover 10, a further (second) cutout AU2 is also present which is provided for accommodating an optical lens LI. Also present between the two cutouts AU1, AU2 is a light-tight barrier BR in order to prevent a part of the light beam L reaching the light receiver 51 directly. The light receiver 51 itself is again arranged on the inner face IS of the circuit substrate 3, its sensor surface F lying opposite an opening OF in the circuit substrate 3 which simultaneously acts as an aperture B.

Figure 11:
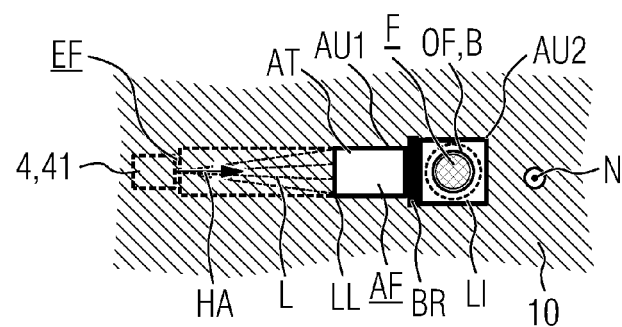
FIG. 11 shows a view from above onto the scattered light smoke detector according to FIG. 10 in the indicated viewing direction XI.

FIG. 11 shows a view from above onto the scattered light smoke detector according to FIG. 10 in the indicated viewing direction XI.

In this view can be seen the two adjacent quadrangular cutouts AU1, AU2, which are separated from one another by the barrier B.

The lens LI accommodated in the second cutout AU2 can also be an integral part of the light receiver 51 itself. In this case the light receiver is preferably arranged on the outer face AS of the circuit substrate 3. The lens LI is then connected upstream of the light receiver in optical terms.

Figure 12:
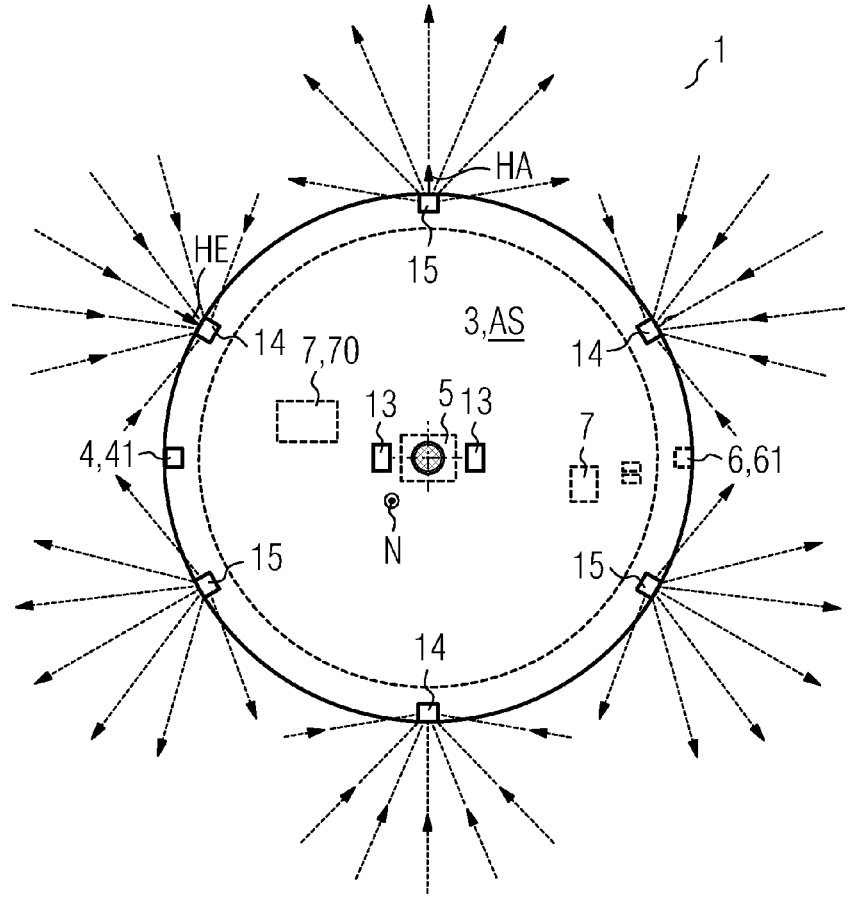
FIG. 12 shows a further embodiment variant of the scattered light smoke detector according to the invention having environment monitoring for flow-shielding objects.

FIG. 12 shows a further embodiment variant of the scattered light smoke detector 1 according to the invention with environment monitoring for flow-shielding objects.

Two first environment light emitters 13 are present by way of example on the outer face AS of the circuit substrate 3, emitting light away from the outer face AS and substantially at right angles to the latter into the environment of the scattered light smoke detector 1. The first environment light emitters 13 emit light preferably in the non-visible infrared range and preferably with a broad, hemispherical emission zone.

Three second environment light emitters 15 are additionally present on the outer face AS of the circuit substrate 3 in a radially outward lying edge region, emitting light substantially radially away from the scattered light smoke detector 1 into the environment of the scattered light smoke detector 1. The second environment light emitters 15 also emit light preferably in the non-visible infrared range. The emission zone is, as shown, preferably fan-shaped in order to emit as much light as possible in a sideways direction to the scattered light smoke detector 1.

First and second environment light emitters 13, 15, as shown in the present example, do not necessarily have to be present.

Additionally arranged in the radially outward lying edge region are three environment light receivers 14, which are provided for the purpose of detecting environment light from a substantially radial direction toward the scattered light smoke detector 1. Viewed in the circumferential direction, they are arranged between the second environment light emitters 15. The second environment light emitters 15 and the environment light receivers 14 can also be combined in an optoelectronic component. In this case six environment light emitters/receivers then result, arranged distributed in the circumferential direction. Apart from the light receiver 5, it is not absolutely necessary for the environment light receivers 14 and/or the direct light receivers 6, as shown in the present example, to be present.

The scattered light smoke detector 1 additionally has an electronic control and evaluation unit 70, which is connected for signal communication purposes to the environment light emitters 13, 15, to the light receiver 5 and to the environment light receivers 14. The control and evaluation unit 70 is configured to activate the respective environment light emitters 13, 15 as well as to capture the electrical signals originating from the light receiver 5, from the environment light receivers 14 and from the direct light receivers 6, which signals correlate with the light pulses reflected from objects, to evaluate said signals with respect to time, and to issue a warning message MO, WARN if a detected object lies within a predefined distance around the scattered light smoke detector 1 and exceeds a predefined minimum signal level.

For enhanced immunity to interference, the environment light emitters 13, 15 preferably emit modulated light, such as e.g. in the range of several KHz to MHz. This can be effected e.g. by the control and evaluation unit 70. In a corresponding manner the receive signals S1-S3 originating from the light receiver 5, from the environment light receivers 14 and from the direct light receivers 6 are filtered with respect to said modulation frequency, such as e.g. by means of a digital filter realized by the control and evaluation unit 70. The filters can also be passive or electronic components.

At higher frequencies in the range of than 1 MHz the phase information of the received signal can also be used to perform a "time-of-flight" analysis. In other words the transit time and hence the path of a light signal transmitted into the environment is determined. An even more accurate assessment of the distance of the interfering object would be conceivable in this way. This distance can therefore be calculated based on the decline in the amplitude of a receive signal S1-S3 due to reflections and/or based on the phase difference between a transmitted light signal and a receive signal S1-S3 in the manner of a time-of-flight measurement.

Figure 13:
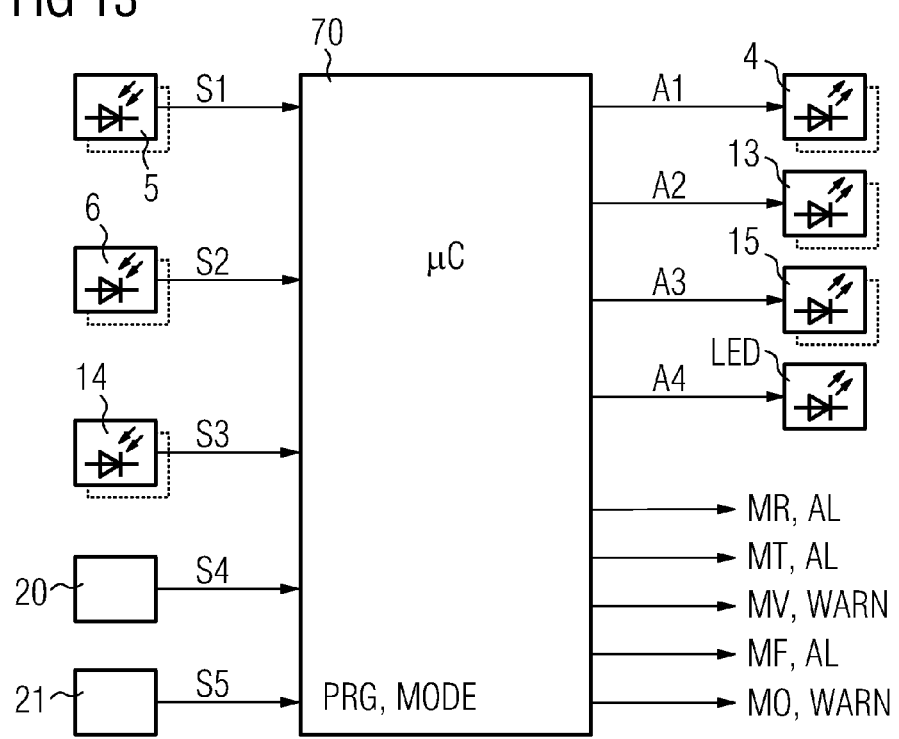
FIG. 13 shows a block diagram of the scattered light smoke detector according to the invention comprising a processor-based control and evaluation unit and having a plurality of connected light emitters and light receivers.

FIG. 13 shows a block diagram of the scattered light smoke detector 1 according to the invention comprising a processor-based control and evaluation unit 70 and having a plurality of connected light emitters 4, 13, 15, LED and light receivers 5, 6, 14.

Reference sign PRG designates a computer program which is suitable for performing the previously described smoke detection and for environment monitoring. The different operating modes selectable on the user side are designated by MODE. These can comprise different parameter sets corresponding to the respective operating mode MODE.

According to the invention the scattered light smoke detector 1 can additionally have a heat sensor 20, such as e.g. a PIR sensor or pyrosensor, or a thermopile or microbolometer heat sensor 20, which is connected for signal communication purposes to the electronic control and evaluation unit 70. The latter can be configured to evaluate a signal S4 captured by the heat sensor 20 for the presence of flicker frequencies characteristic of open fire and if the same are present to issue a flame alarm MF or a fire alarm. AL. The scattered light smoke detector 1 can furthermore have a temperature sensor 21 which is connected for signal communication purposes to the electronic control and evaluation unit 70. The latter can be configured to monitor a signal S5 captured by the temperature sensor 21 for the presence of an unacceptably high temperature and if such a signal is present to issue an excess temperature message MT or a fire alarm AL.

Based on the executed computer program PRG, further alert messages can be issued with MR by means of the control and evaluation unit 70, such as e.g. a smoke message MR, a contamination message MV and an object message, if an object detected as illegal is located in the environment.

LIST OF REFERENCE SIGNS

1 Scattered light smoke detector
2 Housing shell, housing part, receptacle
3 Circuit substrate, printed circuit board
4, 41, 42 Light emitter, LED, IRED
5, 51-53 Light receiver, photodiode, IR photodiode
6, 61, 62 Direct light receiver, photodiode, IR photodiode
7 Components
8 Ring, mounting ring
10 Protective cover
11 Light outcoupling/funnel element
13 First environment light emitter, LED
14 Environment light receiver
15 Second environment light emitter, LED
20 Heat sensor, thermopile, microbolometer, pyrosensor
21 Temperature sensor
70 Electronic control and evaluation unit, processing unit, microcontroller
A1-A4 Output signals
AF Outcoupling surface
AL Alarm message
AS Outer face of the circuit substrate
AS' Outer face of a protective cover, decorative plate or decorative film
AT Light outcoupling part
AU, AU1, Cutout
AU2
B Aperture
BR Barrier
CH Light channel
D, D1, D2 Direct light ray, direct light
DEKO Decorative plate, decorative film
DO Pass-through opening
E Receiving zone, receive sector
EF Incoupling surface
F Sensor surface
HA Main emission direction
HE Main receiving direction IS Inner face of the circuit substrate
K Contour, inner contour, reflecting contour
L, L1, L2 Light beam
LI Lens
LL Light conductor element
LED Optical indicator element, operation indicator
M, M1-M4 Scattered light volume, scattered light center, measurement volume
MF Flame message
MO Object message
MR Smoke message
MT Excess temperature message
MV Contamination message
MODE Operating mode
N Normal, normal direction
OF Optical window, opening, hole, bore
P Particles, smoke particles
PRG Computer program
R Light outcoupling part, ramp
RS Directional ray, light ray in preferred direction
S1-S5 Signals, received signals
SR Inclined surface
SW Sidewall
T1, T2 Input field, touch zone
TO Funnel opening
TR Light funnel
WARN Warning message
α Scattered light angle

What is claimed is:

1. A scattered light smoke detector, comprising:
a housing shell,
a circuit substrate accommodated on the housing shell, and
at least one light emitter and one light receiver arranged on the circuit substrate,
wherein the circuit substrate has an inner face disposed opposite the housing shell and an outer face disposed opposite the inner face,
wherein the light emitter is configured to emit a light beam having a directional ray,
wherein the light emitter and the light receiver are arranged in a scattered light array having a scattered light volume located in the open air outside of the scattered light smoke detector, and
wherein a part of the path traveled by the directional ray between light emitter and the scattered light volume runs parallel to the outer face of the circuit substrate.

2. The scattered light smoke detector of claim 1, wherein the light emitter is arranged and aligned on the circuit substrate such that the light beam emitted by the light emitter runs from an edge of the circuit substrate in the direction of an opposite edge of the circuit substrate.

3. The scattered light smoke detector of claim 1, wherein the light receiver is shielded against direct light from the light emitter, and wherein a main receiving direction of the light receiver points away from the outer face of the circuit substrate.

4. The scattered light smoke detector of claim 3, wherein:
the light receiver has a sensor surface,
the circuit substrate has an optical window for the light receiver, and
the light receiver is arranged and aligned on the inner face of the circuit substrate such that the sensor surface extends parallel to the inner face of the circuit substrate and is located opposite the optical window, such that scattered light from the light emitter is detectable through the optical window acting as an aperture.

5. The scattered light smoke detector of claim 4, wherein the light receiver is a photodiode housed in a flip-chip package or housed in a reverse-gullwing package for direct surface mounting on the circuit substrate.

6. The scattered light smoke detector of claim 3, wherein:
the light receiver has a sensor surface, and
the light receiver is arranged and aligned on the outer face of the circuit substrate such that the sensor surface runs parallel to the outer face of the circuit substrate and scattered light is detectable by the light emitter.

7. The scattered light smoke detector of claim 1, wherein:
the circuit substrate is provided or embodied for attaching a decorative plate or a decorative film on the outer face of the circuit substrate, and
the decorative plate or the decorative film has cutouts or transparent windows for the light receiver or for further optoelectronic components.

8. The scattered light smoke detector of claim 1, comprising a direct light receiver arranged on the circuit substrate,
wherein the direct light receiver is aligned to the light emitter for detecting direct light,
wherein the scattered light volume is located between the light emitter and the direct light receiver, and
wherein the direct light receiver is configured for at least one of contamination monitoring or monitoring a decrease in brightness of the light emitter.

9. The scattered light smoke detector of claim 1, wherein:
the light receiver is arranged and aligned in an edge region of the circuit substrate and at a scattered light angle to the light emitter,
the scattered light volume is located opposite the outer face of the circuit substrate, and
a main receiving direction of the light receiver is parallel to said outer face.

10. The scattered light smoke detector of claim 8, wherein at least one of the light receiver or the direct light receiver is a "sidelooker" photodiode.

11. The scattered light smoke detector of claim 1, comprising a direct light receiver arranged on the circuit substrate,
wherein the direct light receiver is aligned to the light emitter for detecting direct light from the light emitter, and
wherein the scattered light smoke detector has an electronic control and evaluation unit which is connected for communicating signals to the light emitter and the direct light receiver and
wherein the electronic control and evaluation unit is configured to:
activate the light emitter,
capture the signal originating from the direct light receiver,
evaluate the captured signal with respect to a sequence of signal jumps having great signal changes,
compare signal sequences with at least one predefined user-side command sequence, and
in response to detecting a valid command sequence, to switch the scattered light smoke detector to an operating mode associated with the command sequence.

12. The scattered light smoke detector of claim 1, comprising a planar protective cover arranged on the outer face of the circuit substrate, wherein the protective cover covers the circuit substrate,
wherein the protective cover is arranged spaced at a distance from the outer face of the circuit substrate such that a light channel for the light beam emitted by the light emitter results between the outer face of the circuit substrate and an oppositely disposed inner face of the protective cover, wherein the protective cover has a cutout for a light outcoupling/funnel element, wherein the light outcoupling/funnel element has a light funnel for the light receiver as well as a light outcoupling part adjoining the same for coupling out the light beam running from the light emitter in the light channel, and wherein the light outcoupling part is embodied such that the coupled-out light beam extends across the light funnel and beyond into the environment of the scattered light smoke detector.

13. The scattered light smoke detector of claim 1, comprising a planar protective cover that covers the circuit substrate, wherein the planar protective cover is arranged on the outer face of the circuit substrate, wherein the protective cover is arranged spaced at a distance from the outer face of the circuit substrate so that an accommodation space for a light conductor element adjoining the light emitter for forwarding the light beam emitted by the light emitter results between the outer face of the circuit substrate and an oppositely disposed inner face of the protective cover, wherein the protective cover has a cutout for a light outcoupling part of the light conductor element, and wherein the light conductor element is embodied in such a way that the light beam running in the light conductor element is coupled out at an exit surface of the light lead-out part and extends across a receiving zone of the light receiver and beyond into the environment of the scattered light smoke detector.

14. The scattered light smoke detector of claim 1, wherein the light emitter is a "sidelooker" LED.

15. The scattered light smoke detector of claim 1, wherein:

at least one first environment light emitter is arranged on the outer face of the circuit substrate for emitting light away from the outer face and substantially at right angles to the latter into the environment of the scattered light smoke detector, or a plurality of second environment light emitters for emitting light substantially radially away from the scattered light smoke detector into the environment of the scattered light smoke detector are arranged on the outer face of the circuit substrate in a radially outward lying edge region, and the light receiver is arranged on the circuit substrate, wherein the main receiving direction of the light receiver points away from the outer face of the circuit substrate at right angles thereto, and a plurality of environment light receivers are arranged on the outer face of the circuit substrate in the radially outward lying edge region for detecting environment light from a substantially radial direction toward the scattered light smoke detector, and the scattered light smoke detector has an electronic control and evaluation unit configured for communicating signals to the environment light emitters, the light receiver, and the environment light receivers, wherein the control and evaluation unit is configured to:

activate the respective environment light emitters to emit modulated light pulses, capture signals originating from the light receiver and from the environment light receivers, which signals correlate with the modulated light pulses reflected from objects, evaluate the captured signals with respect to time, and issue a warning message if a detected object lies within a predefined distance around the scattered light smoke detector and exceeds a predefined minimum signal level.

16. The scattered light smoke detector of claim 1, comprising a heat sensor thermopile or microbolometer heat sensor arranged on the circuit substrate, wherein the scattered light smoke detector has an electronic control and evaluation unit connected to the heat sensor and configured to:

communicate signals, evaluate a signal captured by the heat sensor for the presence of flicker frequencies characteristic of open fire, and issue a flame alarm in response to detecting the presence of flicker frequencies characteristic of open fire.

17. The scattered light smoke detector of claim 16, wherein the heat sensor comprises a thermopile or microbolometer heat sensor.

* * * * *